(«12») United States Patent
Suh et al.

(10) Patent No.: US 11,628,422 B2
(45) Date of Patent: Apr. 18, 2023

(54) SUPPORTED COPPER CATALYST AND SELECTIVE HYDROGENATION OF FURAN-BASED COMPOUNDS USING THE SAME

(71) Applicant: IUCF-HYU (INDUSTRY—UNIVERSITY COOPERATION FOUNDATION HANYANG UNIVERSITY), Seoul (KR)

(72) Inventors: Young Woong Suh, Seoul (KR); Jin Sung Kim, Pyeongtaek-si (KR)

(73) Assignee: IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 222 days.

(21) Appl. No.: 17/096,835

(22) Filed: Nov. 12, 2020

(65) Prior Publication Data

US 2021/0146341 A1 May 20, 2021

(30) Foreign Application Priority Data

Nov. 15, 2019 (KR) .................. 10-2019-0146415

(51) Int. Cl.
*B01J 23/72* (2006.01)
*B01J 21/04* (2006.01)
*B01J 35/00* (2006.01)
*B01J 35/10* (2006.01)
*C07D 307/42* (2006.01)
*B01J 37/03* (2006.01)
*B01J 37/14* (2006.01)

(52) U.S. Cl.
CPC .............. *B01J 23/72* (2013.01); *B01J 21/04* (2013.01); *B01J 35/0053* (2013.01); *B01J 35/1009* (2013.01); *B01J 35/1014* (2013.01); *B01J 35/1019* (2013.01); *B01J 35/1023* (2013.01); *B01J 35/1061* (2013.01); *B01J 37/036* (2013.01); *B01J 37/14* (2013.01); *C07D 307/42* (2013.01)

(58) Field of Classification Search
CPC ....................................................... B01J 23/72
USPC ........................................................ 549/503
See application file for complete search history.

(56) References Cited

FOREIGN PATENT DOCUMENTS

| CN | 104148086 A | 11/2014 |
|----|-------------|---------|
| CN | 110339841 A | 10/2019 |
| JP | 2013510714 A | 3/2013 |

OTHER PUBLICATIONS

Ohyama et al., Selective hydrogenation of 2-hydroxymethyl-5-furfural to 2,5-bis(hydroxymethyl)furan over gold sub-nano clusters, RSC Advances, pp. 1033-1036, Nov. 5, 2012.
Tamura et al., "Rapid synthesis of unsaturated alcohols under mild conditions by highly selective hydrogenation" Chemical Communications, May 8, 2013.
Cao et al., "Catalytic synthesis of 2,5-bis-methoxymethylfuran: A promising cetane number improver for diesel" Applied Catalysis A: General, vol. 481, pp. 49-53, Jul. 4, 2014.
Chatterjee et al., "Selective hydrogenation of 5-hydroxymethylfurfural to 2,5-bis-(hydroxymethyl)furan using Pt/MCM-41 in an aqueous medium: a simple approach" Green Chemistry, pp. 4734-4739, Aug. 20, 2014.
Hu et al., "Catalytic Advances in the Production and Application of Biomass-Derived 2,5-Dihydroxymethylfuran" ACS Catalysis, pp. 2959-2980, Feb. 28, 2018.
Zhang et al., "Methods in the Synthesis and Conversion of 2,5-Bis-(hydroxylmethyl) furan from Bio-derived 5-Hydroxymethylfurfural and its Great Potential in Polymerization" Bioresources, pp. 7137-7154, May 27, 2018.
Korean Office Action issued in corresponding application No. 10-2019-0146415, dated Dec. 14, 2020.

*Primary Examiner* — Taofiq A Solola
(74) *Attorney, Agent, or Firm* — Maschoff Brennan

(57) ABSTRACT

Disclosed are a catalyst including copper (Cu) particles having specific properties as an active metal dispersed and supported on an alumina support, a method of preparing the same, and a method of hydrogenating furan-based compounds such as 5-(hydroxymethyl)furfural (HMF) derived from biomass with a high selective conversion and high efficiency using the catalyst.

19 Claims, 5 Drawing Sheets

SUPPORTED COPPER CATALYST AND SELECTIVE HYDROGENATION OF FURAN-BASED COMPOUNDS USING THE SAME

BACKGROUND OF THE INVENTION

Field of the Invention

The present disclosure relates to a supported copper catalyst and a method for hydrogenating furan-based compounds using the same. More specifically, the present disclosure relates to a catalyst comprising copper (Cu) particles having specific properties as an active metal dispersed and supported on an alumina support, a method of preparing the same, and a method of hydrogenating furan-based compounds such as 5-(hydroxymethyl)furfural (HMF) derived from biomass with a high selective conversion and high efficiency using the catalyst.

Description of the Related Art

A great deal of research has recently been actively conducted to at least partly replace petroleum energy sources, which has supported the development of mankind, with biomass due to their problems associated with non-renewability, unequal distribution, and environmental pollution.

In a broad sense, biomass may encompass all substances derived from biological origins, and in a narrow sense, it may mean substances derived from vegetable sources such as corn, soybeans, flax seeds, sugarcane and palm oil. Biomass also may encompass all living organisms or metabolic byproducts as elements in a carbon cycle. Such biomass is reported to be widely used in the production of various biofuels and biochemicals (or platform compounds).

An example of the most widely used biomass is lignocellulosic biomass, which can be widely used in the production of biofuels and biochemicals. Lignocellulosic biomass contains cellulose, hemicellulose and lignin bound in a complex and rigid structure. Recently, furan-based compounds formed through saccharification of lignocellulosic biomass have attracted a great deal of attention. In particular, a method using 5-(hydroxymethyl)furfural (HMF), produced by dehydrating fructose, which is a monosaccharide derived from biomass, has been actively studied.

HMF is an intermediate substance that can be usefully applied to the production of various high value-added compounds and fuel oils through a simple reaction, such as that depicted in Reaction Scheme 1 below, and specifically, 2,5-dimethylfuran (DMF), ethyl levulinate (EL), 5-(alkoxymethyl)furfurals (AMFs), γ-valerolactone (GVL), 2,5-bis(alkoxymethyl)furans (BAMFs) and the like are being studied, and among them, AMF is attracting particular attention due to the high energy density thereof and the decreased negative effect on diesel engines. In addition, high-value-added compounds such as levulinic acid, 2,5-furandicarboxylic acid (FDCA) and 2,5-diformylfuran (DFF) can be prepared from HMF.

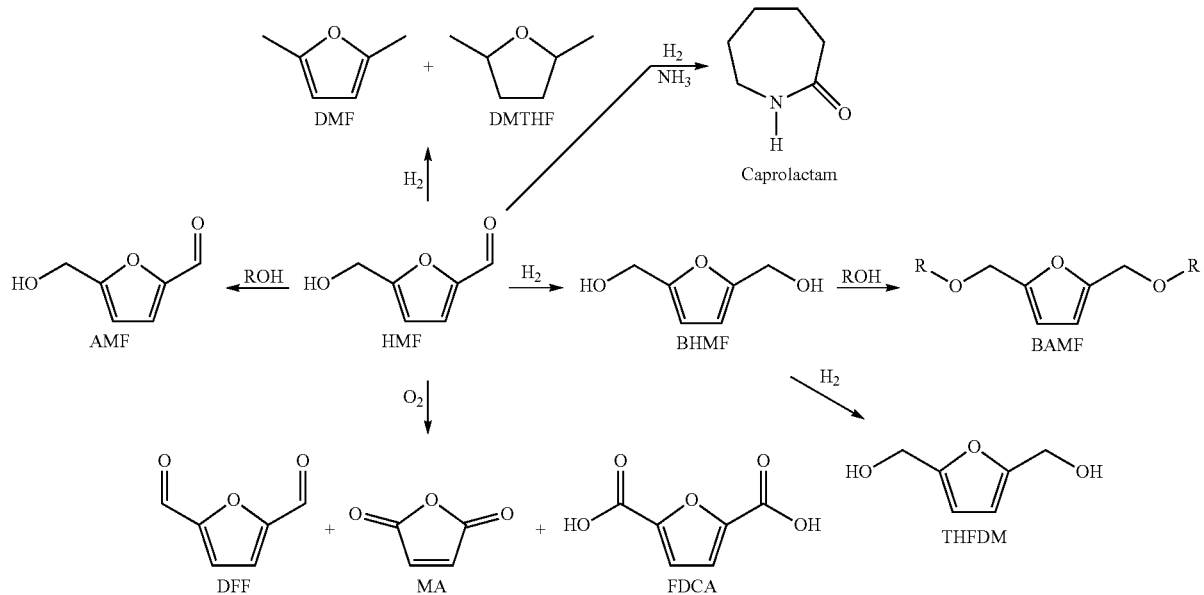

[Reaction Scheme 1]

As shown in the Reaction Scheme above, bis-2,5-hydroxymethylfuran (BHMF) can be prepared by converting the aldehyde functional group of HMF into a hydroxyl functional group through hydrogenation. BHMF is a diol having hydroxyl functional groups at both terminals thereof and can be applied to the preparation of environmentally friendly polymers through polymer synthetic processes. As such, BHMF is environmentally and commercially important in that polymers can be prepared from biomass-derived chemicals instead of conventional petroleum-based raw materials. It is expected that interest in technology for preparing BHMF from HMF will continue to increase (ACS Catal., 8 (2018) 2959-2980, BioResources, 13 (2018) 7137-7154).

In the reaction for converting HMF to BHMF through selective hydrogenation, it is required to secure a high conversion and selectivity. In particular, it is needed to suppress side reactions, such as the generation of 2,5-dimethyl furan (DMF) and 2,5-bis(hydroxymethyl)-tetrahydrofuran, caused by excessive hydrogenation of HMF. In addition, it is necessary to realize good hydrogenation efficiency even at low temperatures, as well as improvement in long-term catalyst stability.

Currently, catalysts for hydrogenating HMF to BHMF may be classified into noble-metal-based catalysts and non-precious-metal-based catalysts. In this regard, noble-metal-based catalysts such as Pt/alumina catalysts (Catal. 2014, 313, 70), Au/alumina catalysts (RSC Adv., 2013, 3, 1033-1036), Ir/ReOx catalysts (Chem. Commun., 2013, 49, 7034-7036), and Pt/MCM-41 catalysts (Green Chem., 2014, 16, 4734-4739) have been developed, and these catalysts are reported to exhibit high catalytic activity (i.e., conversion and selectivity) at low temperatures. There is limitation in commercial applicability thereof due to the use of expensive precious metals. Meanwhile, Cu/silica catalysts (Appl. Catal., A 2014, 481, 49) and the like are known as non-precious-metal-based catalysts that exhibit lower catalytic activity than noble-metal-based catalysts, may cause generation of byproducts, and require energy to be consumed to maintain the temperature.

Therefore, there is a need to develop hydrogenation catalysts that use non-precious metals and exhibit high activity even at low temperatures.

SUMMARY OF THE INVENTION

Therefore, the present disclosure provides a non-precious metal-based catalyst that is suitable for selective hydrogenation of furan-based compounds and is advantageous for commercial application, and a method of preparing the same.

The present disclosure also provides a hydrogenation process for preparing BHMF from HMF at a low temperature at high conversion and high selectivity using a non-precious metal-based catalyst with improved properties.

In accordance with a first aspect of the present disclosure, there is provided a method for preparing bis-2,5-hydroxymethylfuran (BHMF) from 5-hydroxymethylfurfural (HMF), which comprises:

feeding a feedstock containing 5-hydroxymethylfurfural (HMF); and hydrogenating the feedstock in a liquid reaction medium using a catalyst comprising a mesoporous alumina-containing support and particles of copper as an active metal on the mesoporous alumina-containing support to convert the 5-hydroxymethylfurfural (HMF) in the feedstock to bis-2,5-hydroxymethylfuran (BHMF), wherein the catalyst has (i) a copper particle size of 15 nm or less, (ii) a copper content of 15 to 40% by weight based on the element, and (iii) a copper specific surface area ($S_{Cu}$) of 6 to 35 $m^2/g$, and (iv) a pore size of 2 to 6 nm.

In accordance with a second aspect of the present disclosure, there is provided a method of preparing a hydrogenation catalyst, which comprises:

a) performing a solid-state reaction in the absence of a solvent while applying external energy to a mixture containing at least one alumina precursor, at least one copper precursor and a base to form a catalytic solid in a form of a gel, and b) thermally treating the catalytic solid under an oxygen-containing atmosphere at a temperature of 300 to 800° C. to support copper particles in a form of oxide on a mesoporous alumina-containing support, wherein the hydrogenation catalyst has (i) a copper particle size of 15 nm or less, (ii) a copper content of 15 to 40% by weight based on the element, and (iii) a copper specific surface area ($S_{Cu}$) of 6 to 35 $m^2/g$, and (iv) a pore size of 2 to 6 nm.

In an exemplary embodiment, the method may further comprise c) reducing the copper particles in the form of oxide obtained in step b).

In accordance with a third aspect of the present disclosure, there is provided a hydrogenation catalyst, which comprises:

a mesoporous alumina support; and particles of copper as an active metal on the mesoporous alumina-containing support, wherein the hydrogenation catalyst has (i) a copper particle size of 15 nm or less, (ii) a copper content of 15 to 40% by weight based on the element, (iii) a copper specific surface area ($S_{Cu}$) of 6 to 35 $m^2/g$, and (iv) a pore size of 2 to 6 nm.

In an exemplary embodiment, the hydrogenation catalyst may have a specific surface area (BET) of 330 to 700 $m^2/g$.

BRIEF DESCRIPTION OF THE DRAWINGS

The above and other features and advantages of the present disclosure will be more clearly understood from the following detailed description taken in conjunction with the accompanying drawings, in which.

DETAILED DESCRIPTION OF THE INVENTION

Figure 1:
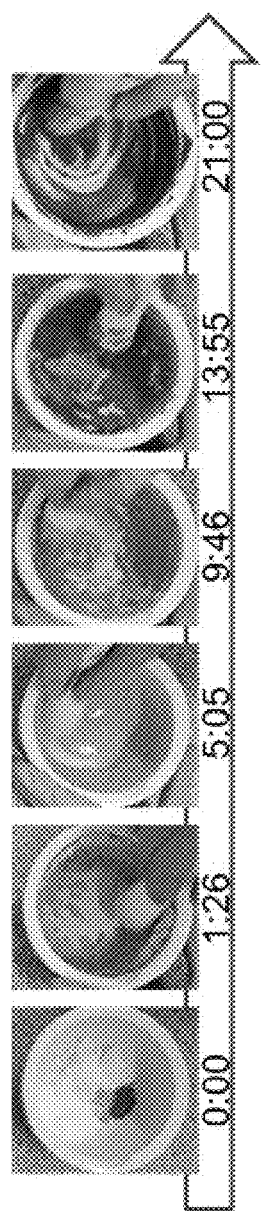
FIG. 1 is an image showing phase change of precursors during a series of steps for preparing a hydrogenation/dehydrogenation catalyst according to Example.

The present invention can be accomplished in its entirety based on the following description. The following description should be understood as describing preferred embodiments of the present invention, but the present invention is not necessarily limited thereto. In addition, it should be understood that the accompanying drawings are provided merely for better understanding of the present invention, and the present invention is not limited thereto.

Terms used herein may be defined as follows.

The term "biomass" generally means an organic material produced by photosynthesis, but may be interpreted to include organic wastes such as animal manure and food wastes. In a broad sense, biomass includes various biological resources known in the art, e.g., corn, soybean, linseed, sugarcane and palm oil, including vegetable biomass, specifically cellulose, hemicellulose and/or lignin (i.e., lignocellulose), and more specifically includes rice straw, wheat straw, starch-containing grains, corn cobs, corn stalks, rice husks, paper products, wood, sawdust, agricultural waste, grass, sugarcane, cotton, flax, bamboo, manila hemp, algae, fruit peels, seaweed, oil palm waste, stems, roots and leaves of plants, and the like). More specifically, the biomass includes carbohydrates obtained from the biomass described above, such as starch and sugars, specifically monosaccharides (glucose, fructose, galactose, xylose, arabinose, mannose, etc.), disaccharides (sucrose, lactose, maltose, cellobiose, etc.), and other (oligo) saccharides.

The term "heterogeneous catalyst" may mean a catalyst that exists in a phase different from that of a reactant during a catalytic reaction, for example, a catalyst that is not dissolved in a reaction medium. In the case of a heterogeneous catalyst, in order for the reaction to occur, at least one reactant should be diffused and adsorbed onto the surface of the heterogeneous catalyst, and after the reaction, the product should be desorbed from the surface of the heterogeneous catalyst.

The term "support" may mean a material (typically a solid material) having a high specific surface area, to which a catalytically active component is attached.

The term "hydrogenation" may refer to a reaction that increases the content of hydrogen in the compound by chemically adding hydrogen to at least a part of the compound by bringing the compound into contact with a catalyst in the presence of hydrogen (or supplied hydrogen).

The term "crystalline" may mean any solid material that is typically arranged to have a lattice structure (e.g., a three-dimensional order) and can be generally specified by X-ray diffraction analysis (XRD), nuclear magnetic resonance analysis (NMR), differential scanning calorimetry (DSC) or a combination thereof.

The term "impregnation" may mean a method of preparing a catalyst by impregnating a separately prepared support with a solution in which a catalyst precursor is dissolved and then drying and/or firing (or reduction) the resulting support, if necessary.

The term "salt" may generically mean a compound in which a metal cation is bonded to an inorganic anion or an organic anion.

Hydrogenation Catalyst

According to an embodiment of the present disclosure, provided is a catalyst (i.e., heterogeneous catalyst) suitable for hydrogenation reaction, specifically the selective hydrogenation of converting a furan-based compound such as HMF or derivative thereof (a compound containing a 5-membered ring having one heteroatom, that is, a furan ring) to BHMF.

In this regard, the hydrogenation catalyst is a supported catalyst containing entirely copper as an active metal on the mesoporous alumina-containing support. Here, the copper may be in the form of crystallites that are dispersed and supported on the support in the form of nano-sized metal particles, that is, metal clusters. According to an exemplary embodiment, (111), (200) and (220) planes can be observed at 2θ of 43.3°, 50.4° and 74.1°, respectively, from the active copper crystals.

According to an exemplary embodiment, the crystal (particle) size of copper in the catalyst can be determined using the Scherrer equation and is, for example, about 15 nm or less, specifically about 1 to about 12 nm, and more specifically about 1.3 to about 10 nm. When the crystal size of the active metal is excessively large, a reaction efficiency decreases due to the decrease in the degree of dispersion of the metal supported on the support, while when the crystal size of the active metal is excessively small, the number of active sites, on which the reactant is adsorbed, decreases and thus the frequency of adsorption decreases. As such, it is preferable that the crystal size of the active metal be adjusted within the range as stated above, but may be slightly changed depending on the reaction conditions and the like.

In order to provide good hydrogenation activity, the hydrogenation catalyst according to an exemplary embodiment can exhibit a high copper specific surface area, in which fine copper particles are uniformly dispersed on an alumina-based support in an appropriate amount.

In this regard, when the content of copper is less than a desired level, the conversion of HMF as a reactant may be decreased and thus the yield of BHMF as a target compound may be decreased, since it is difficult to secure a desired copper specific surface area. However, it needs to consider the following aspects when increasing the copper content to a certain level or more.

In general, a heterogeneous supported catalyst exhibits decreased activity as the amount of active metal that is supported increases, because the degree of distribution of the active metal decreases. In contrast, the catalyst according to an embodiment can exhibit the increased specific surface area of copper while the amount of supported copper increases to a certain level, and thus can provide better hydrogenation activity even with a relatively high amount of copper. Specifically, nano-sized copper particles are entangled with the microstructure of the alumina support and thus enable the active metal to be dispersed well, although the amount of supported copper is increased to a certain level, and thereby improve the catalytic activity of the reactant, unlike the conventional supported catalysts (for example, catalysts including an active metal locally attached to the support surface by an impregnation method or the like). In particular, because copper is inexpensive compared to expensive metal ingredients such as precious metals, it is advantageous to improve catalytic activity by increasing the copper content as much as possible and by simultaneously suppressing deactivation factors such as aggregation or growth of nanoparticles (i.e., uniformly dispersing a large amount of active ingredients to maximize the exposure thereof). The copper particles thus obtained are remarkably small (specifically, about 15 nm or less, as described above, and the degree of dispersion thereof can be significantly increased. In this aspect, the catalyst according to the present embodiment can provide an advantage of improving the properties of catalysts, which seemingly contradict with each other, at the same time.

However, even if it is possible to increase the copper content, when the copper content exceeds a certain level, agglomeration (aggregation) of copper may occur. In consideration of this, the content of the copper particles in the catalyst may range from about 15 to about 40% by weight, specifically about 18 to about 35% by weight, and more specifically about 20 to about 30% by weight, based on element.

In addition, in the catalyst according to an embodiment, a relatively large amount of copper is distributed on the support with a high degree of dispersion and thus the copper has a high specific surface area, so that the reactant HMF can easily access the catalytic sites having a hydrogenating function, specifically copper particles (or clusters).

In this regard, the specific surface area ($S_{Cu}$) and dispersion degree ($D_{Cu}$) of copper can be measured by $N_2O$—RFC (reactive frontal chromatography). This measurement technique is described in detail in Angew. Chem. Int. Ed., 53 (2014) 7043-7047, which is incorporated herein by reference in its entirety.

In an exemplary embodiment, the specific copper surface area of the catalyst may range from, for example, about 6 to about 35 $m^2/g$, specifically about 10 to about 25 $m^2/g$, and more specifically about 14 to about 16 $m^2/g$. Further, the degree of dispersion of copper may be fairly high, for example in the range of about 4 to about 16%, specifically about 6 to about 15%, and more specifically about 10 to about 14%.

It should be noted that the supporting properties of copper are significantly increased compared to the specific surface area and dispersion degree of copper supported on the alumina support by conventional techniques such as coprecipitation and impregnation.

Meanwhile, in the present embodiment, the support of the hydrogenation catalyst may be an alumina-containing support. Such an alumina support in a catalyst is mesoporous alumina, which can typically exhibit ink-bottle or channel-type pore connectivity. In the hydrogenation reaction, the support can exhibit a relatively high surface area, high packing density, thermal stability, physical strength and regenerability. In particular, it is worth noting that the copper particles are well bound while being entangled with the surrounding or neighboring aluminum particles, thereby firmly maintaining the mesoporous structure.

According to an exemplary embodiment, the specific surface area (BET) of the support in the catalyst is, for example, about 330 to about 700 $m^2/g$, specifically about 380 to about 600 $m^2/g$, and more specifically about 430 to about 500 $m^2/g$. This specific surface area may be a level suitable for uniform dispersion while supporting a certain amount or more of nano-sized copper particles, which are active metals.

According to an exemplary embodiment, the pore volume of the support in the catalyst may range from, for example, about 0.3 to about 0.8 $cm^3/g$, specifically about 0.45 to about 0.65 $cm^3/g$, and more specifically about 0.53 to about 0.57 $cm^3/g$. In addition, the pore size of the support in the catalyst may range from, for example, about 2 to about 6 nm, specifically about 3 to about 4.5 nm, and more specifically about 3.6 to about 3.8 nm.

In addition, the acidity of the catalyst ($N_{acid}$) can be obtained through a temperature-programmed adsorption test of $NH_3$ ($NH_3$-TPD). In this regard, the catalyst according to an embodiment may exhibit acidity in the range of, for example, about 12 to 40 μmol/g, specifically about 18 to about 34 μmol/g, and more specifically about 22 to about 30 μmol/g, which are provided for illustrative purposes. However, the catalyst according to an embodiment may exhibit higher acidity than the catalyst prepared by impregnation, and in particular, the decrease in acidity is relatively low even after reaction for a long time. Moreover, in the case of a catalyst prepared by co-precipitation, a catalyst having somewhat high acidity can be realized, but as the target reaction continues, the decrease in acidity is great compared to the catalyst according to the present embodiment.

Meanwhile, the copper particles in the catalyst may be present in a reduced state (specifically, in a reduced state and/or a partially reduced state). This reduced state can be obtained by reducing the oxidized (calcined) catalyst. According to an exemplary embodiment, the copper in the catalyst may be in an elemental state ($Cu^0$), but may be present in a combination of an elemental state ($Cu^0$) and a partially reduced state ($Cu^+$). In this case, the ratio of the elemental state ($Cu^0$) to the partially reduced state ($Cu^+$) may be, for example, at least about 85%, specifically at least about 95%, and more specifically at least about 98%, but this is provided only for illustrative purposes. As described above, when not only elemental copper but also partially reduced copper is contained, higher acidity can be obtained than a catalyst containing only elemental copper (mainly, a catalyst prepared according to a conventional method such as impregnation).

According to an exemplary embodiment, the shape of the catalyst is not particularly limited, but it may be applied to a molded product having a shape such as a ball shape, a tablet shape, a granule shape, a pellet shape or a cylindrical shape in consideration of stability and efficiency of the catalyst. Here, the size (or diameter) of the catalyst may range from, for example, about 0.1 to about 10 mm, specifically about 0.5 to about 5 mm, and more specifically about 1 to about 3 mm, but this is provided only for illustrative purposes.

As such, in the catalyst according to an embodiment, copper having a smaller size is distributed at a high dispersion degree on a mesoporous alumina-containing support and thereby provides a larger copper surface area and thus an increased number of active hydrogenation sites, to thereby enable HMF, the reactant for hydrogenation, to effectively access to the active sites. These advantages are supposed to stem from easier diffusion of HMF due to the mesoporous properties of the catalyst and the preferential adsorption of HMF to copper particles that are active metals.

Preparation of Hydrogenation Catalyst

According to another embodiment of the present disclosure, provided is a method of preparing a catalyst having excellent hydrogenation activity, specifically a catalyst for selective hydrogenation of furan-based compounds.

In this regard, the present inventors have found that it is difficult to realize the properties of the copper particles suitable for the intended hydrogenation (for example, the size of the copper particles, the copper content, the surface area, etc.) and the pore characteristics of the support using the most typically applied impregnation method in the preparation of a metal/alumina supported catalyst in the related art.

In consideration of this, by uniformly dispersing copper particles having specific properties on an alumina-containing support through a simple method of reacting a copper precursor and an alumina precursor in a single step without using a solvent and subsequently performing heat treatment (specifically, heat treatment in an oxygen-containing atmosphere), a catalyst capable of conducting a hydrogenation at a high conversion and selectivity can be prepared.

Furthermore, in order to improve the stability of the catalyst, a strong interaction between the active metal and the support is required, and it is preferable to uniformly disperse and support the active metal on the support. As a metal-oxide-based support, an alumina support is known to be effective in terms of catalytic stability because it is intrinsically strongly bonded to a precursor of an active metal. However, in the case of gamma-alumina, which is widely used as an alumina support by impregnation, it is difficult to disperse the copper particles with a uniform and high specific surface area for maximizing hydrogenation activity.

In addition, when copper is supported by impregnation using mesoporous alumina having a relatively high specific surface area as a support, there is a limitation in the extent to which the specific surface area of the final catalyst can be increased due to the nature of the production technique, and in particular, it is difficult to uniformly disperse copper as an active metal on nano-sized level, and it is difficult for the reactant to access the copper particles, that is, the active sites, with high frequency.

According to one embodiment, first, a precursor mixture including at least one alumina precursor, at least one copper precursor and a base is prepared.

For example, the precursor mixture may be prepared by mixing three ingredients simultaneously. Alternatively, the precursor mixture may be prepared by first mixing two of the three ingredients and then adding the remaining one. For example, the alumina precursor and the base may be mixed first, and then a copper precursor may be added thereto and mixed therewith.

According to an exemplary embodiment, the copper precursor may be an organic or inorganic acid salt of copper, a complex of copper, or a combination thereof. Such a copper precursor may be, for example, a $Cu^{2+}$ precursor. For example, the copper precursor may be copper hydroxide phosphate, copper nitrate, copper sulfate, copper acetate, copper formate, copper (II) chloride, copper iodide or the like, and may be used alone or in combinations of two or more types. However, the types of the copper precursor that are listed above may be exemplary. More typically, the copper precursor may be used in the form of copper nitrate and/or a hydrate thereof.

In addition, the alumina precursor may be an organic or inorganic acid salt, an alkoxide or a complex of aluminum, or a combination thereof, and representative examples thereof may include at least one selected from the group consisting of aluminum acetate, aluminum acetylacetonate, aluminum bromide, aluminum t-butoxide, aluminum sec-butoxide, aluminum pentoxide, aluminum ethoxide, aluminum isopropoxide, aluminum tributoxide, aluminum chloride, aluminum bromide, aluminum iodide, aluminum sulfate, aluminum nitrate and a hydrate thereof. More specifically, aluminum nitrate and/or a hydrate thereof may be used.

According to an exemplary embodiment, the base may include at least one selected from the group consisting of ammonium carbonate, ammonium bicarbonate, ammonium chloride, ammonium oxalate, ammonium sulfate, ammonium hydroxide, ammonium nitrate, lithium hydroxide, sodium hydroxide, potassium hydroxide, calcium hydroxide and magnesium hydroxide, and more specifically, may be ammonium bicarbonate. The reason for using such a base is that, when forming a metal oxide from an acidic metal precursor, a neutralization reaction, in which the base component is added and precipitated to produce the metal salt and water, occurs.

According to an exemplary embodiment, the molar ratio of the copper precursor to the base in the precursor mixture may range from, for example, about 0.02 to about 0.1, specifically about 0.03 to about 0.08, and more specifically about 0.04 to about 0.06. When the amount of the base that is used is excessively small or large, the time required to form the gel, which is the final stage of synthesis, becomes shorter or longer, thus making it difficult to form metal oxide having a desired crystalline phase and affecting catalyst properties such as a specific surface area, the dispersion degree of metal, the particle size, and the like. However, the range can be changed according to the type of precursor and the base.

In addition, the mixing ratio between the copper precursor and the alumina precursor in the precursor mixture may be determined according to the amount of copper that is supported on the alumina support of the catalyst described above.

According to one embodiment, the reaction may be performed while applying external energy in the process of preparing the above-described precursor mixture or after forming a physical mixture thereof. At this time, it should be noted that, unlike the conventional support method such as impregnation, only the reaction between the solid-state precursors is performed, without using a solvent.

In the case of adopting a solid-state reaction during the step of catalyst synthesis, stronger interaction between metal precursors (precursor of active metals (copper) and precursor of inorganic metal oxide (alumina)) can be induced, compared to the method including preparing a liquid metal precursor solution and then bringing the solution into contact with a porous inorganic metal oxide support (specifically, alumina) to fix or attach the metal precursor to the pores of the support. As a result, the phenomenon of agglomeration (or aggregation) of the metal particles significantly decreases even after the solid-state reaction.

The solvent-free preparation method according to the present embodiment can realize the properties and amount of copper particles effective for selective hydrogenation of furan-based compounds or derivatives such as HMF on mesoporous alumina supports having a high specific surface area, and further provide excellent catalytic activity even at low temperatures through improved interaction between metal ingredients. This corresponds to further improved properties compared to what is achieved by the conventional impregnation methods.

According to one embodiment, the external energy applied to perform the solid-state reaction between the three ingredients (components) described above is typically physical or mechanical energy, and may be, for example, friction energy applied during milling, grinding, pulverizing or the like, specifically frictional energy applied using a ball mill. However, these are provided for illustrative purposes, and any form of external energy may be used without particular limitation, as long as it can induce a reaction between the copper precursor and the alumina precursor in the absence of a solvent.

According to an exemplary embodiment, the solid-state reaction under the application of external energy may be performed for, for example, about 5 to about 40 minutes, specifically about 10 to about 30 minutes, and more specifically about 13 to about 25 minutes. At this time, as the solid-state reaction between the precursors progresses, a gel-like catalytic solid may be formed. Specifically, in the process of solid-state reaction or mixing under the application of external energy (e.g., frictional energy), the base is partially or completely decomposed, and when the metal precursor takes the form of a metal salt, the anion or anion species bound to a metal cation may be substituted with a hydroxide group. In this process, gases derived from precursors and the base may be released. For example, when ammonium bicarbonate is used as the base, a large amount of carbon dioxide may be generated. As the reaction proceeds in the presence of generated gas, the precursors form a gel, its rigidity increases due to solidification, and then a gel is formed again. As a result, a catalytic solid in the form of a gel can be obtained.

Then, a step of converting the gel-like catalytic solid to an oxide by heat treatment, that is, calcining, under an oxygen-containing atmosphere (specifically, under an ambient atmosphere) may be performed. Through this heat treatment step, nanoparticles (or crystals) of copper may be homogeneously dispersed within the pores of the mesoporous alumina support. At this time, copper crystals or particles may be typically supported in the form of an oxide by heat treatment under an oxygen atmosphere. In addition, through heat treatment under an oxygen atmosphere, a porous and pore-to-pore connection structures can be developed and mesoporous alumina having enhanced stability can be formed.

According to an exemplary embodiment, the heat treatment may be performed under a temperature condition of, for example, about 300 to about 800° C., specifically about 350 to about 700° C., and more specifically about 400 to about 600° C. At this time, the heating rate can be, for example, controlled within about 1 to about 10° C./min, specifically about 1.5 to about 5° C./min, and more specifically about 2 to about 4° C./min. For example, the heat treatment time may be controlled within a range of, for example, about 1 to about 24 hours, specifically about 3 to about 10 hours, and more specifically about 4 to about 6 hours.

Meanwhile, after heat treatment under an oxygen atmosphere, a reduction treatment may be further performed in order to activate the catalyst for the hydrogenation, which is the final use thereof. According to an exemplary embodiment, as the gas for the reduction treatment, hydrogen, carbon monoxide, methane, a combination thereof, or a mixture of a diluent gas therewith may be used, and more typically, reduction treatment may be performed under a hydrogen atmosphere.

For example, the reduction treatment temperature may be within the range of about 180 to about 400° C. (specifically about 200 to about 350° C., and more specifically about 250 to about 320° C.). In this case, the heating rate may be, for example, within the range of about 1 to about 10° C./min, and specifically about 4 to about 6° C./min. In addition, the reduction treatment time is not particularly limited, but may be determined within a range of, for example, about 0.5 to about 10 hours, specifically about 1 to about 5 hours. In addition, the pressure during the reduction treatment (partial pressure of the reducing gas) is not particularly limited, and is, for example, in the range of about 1 to about bar, specifically about 1.5 to about 4 bar, more specifically about 2 to about 3 bar. The reduction treatment conditions described above are provided for illustrative purposes, and the present disclosure is not necessarily limited thereto. In this way, through the reduction treatment, a catalyst in which copper in a reduced state (specifically, an elemental state and/or a partially reduced state) is supported on a mesoporous alumina support can be prepared.

Preparation of BHMF Through Selective Hydrogenation of HMF

According to another embodiment of the present disclosure, the hydrogenation for converting HMF to BHMF may be performed using the above-described copper-supported alumina catalyst in a liquid medium.

According to one embodiment, as a medium for hydrogenation of HMF, a polar solvent, specifically, a solvent having a hydroxy group such as water and/or an aliphatic alcohol-based solvent, may be used. According to an exemplary embodiment, a straight-chain alcohol may be used as the reaction medium. According to an exemplary embodiment, as the reaction medium, for example, at least one alcohol selected from the group consisting of an alcohol having 5 or fewer carbon atoms, specifically an alcohol having about 1 to about 4 carbon atoms, more specifically methanol, ethanol or 1-propanol, may be used. A linear alcohol is more polar than a branched alcohol or a non-polar organic solvent (e.g., hexane or tetrahydrofuran (THF)) as the reaction medium. Thus, the carbonyl bond is supposed to be further polarized in such a solvent so that hydrogen absorbed at the copper active site can easily attack the carbonyl group of HMF.

According to an exemplary embodiment, a feedstock containing HMF is provided, and the HMF-containing feedstock is fed to a polar solvent. Thereafter, HMF in the feedstock is converted to BHMF through a selective hydrogenation reaction under a hydrogen atmosphere or in the presence of supplied hydrogen.

According to an exemplary embodiment, the weight ratio of HMF to liquid reaction medium may range from about 1:10 to about 1:50, specifically from about 1:20 to about 1:40, and more specifically from about 1:25 to about 1:35. In addition, the weight ratio of HMF:catalyst in the reaction system may range from about 1:0.05 to about 1:0.8, specifically from 1:0.15 to about 1:0.6, and more specifically from about 1:0.2 to about 1:0.5. Regarding the weight ratio of the catalyst, as long as it is performed under a low reaction temperature (for example, about 70° C.), even if the amount of the catalyst is increased, relatively few byproducts are generated. However, as the amount of the catalyst that is used decreases, the economic efficiency of the reaction can be improved, so it may be advantageous to set the weight ratio of HMF:catalyst as low as possible within the aforementioned range as long as good catalytic activity is realized, and it may be particularly advantageous to set the weight ratio to 1:0.2.

According to an exemplary embodiment, the hydrogenation temperature may be set within the range of, for example, about 60 to about 110° C., specifically about 70 to about 105° C., and more specifically about 70 to about 100° C., and such a reaction temperature is significantly lower than the reaction temperature (about 120° C. or higher) set in the conventionally known same reaction (synthesis of BHMF through selective hydrogenation of HMF). When the reaction temperature is below a certain level, the conversion of HMF and the selectivity to BHMF decrease rapidly, and when the reaction temperature exceeds the appropriate range, the conversion of HMF increases, but byproducts are inevitably produced due to the low selectivity to BHMF. Thus, it may be advantageous to appropriately adjust the reaction temperature in consideration of other reaction conditions within the above-described range.

Meanwhile, the reaction pressure (hydrogen pressure or hydrogen partial pressure) can be adjusted within a range of, for example, about 15 to about 100 bar, more specifically about 20 to about 80 bar, and particularly specifically about 30 to about 60 bar. In this regard, as long as the reaction is performed under a hydrogen pressure of a certain level (e.g., about 50 bar), the influence of the hydrogen pressure relative to the reaction temperature is relatively low.

In addition, the hydrogenation may be performed for, for example, about 1 to about 24 hours, specifically about 2 to about 20 hours, and more specifically about 3 to about 18 hours, but this can be changed according to other reaction conditions, and thus is considered to be provided for illustrative purposes. For example, as the hydrogenation proceeds, the amount of hydrogen used by the reactant (reaction mixture) is observed, and the hydrogenation reaction is terminated when the theoretical amount of hydrogen is absorbed.

When the hydrogenation is complete, the catalyst can be separated and recovered from the hydrogenation product. In addition, optionally, after isolating and removing byproducts or impurities (e.g., AMFA, MFA, etc.) contained in the product, BHMF may be recovered. For example, in order to separate BHMF from the hydrogenation product, at least one separation means selected from distillation, extraction, use of a separation membrane and the like may be employed.

According to this embodiment, it is possible to achieve high conversion of HMF and high selectivity to BHMF in the feedstock through a hydrogenation system using a copper/alumina catalyst in a liquid medium. In this regard, for the catalyst used in this embodiment, the turnover number (TON) may be, for example, about 20 to about 80 (specifically about 30 to about 60, more specifically about 35 to about 50), and the turnover frequency (TOF) may be, for example, range from about 6 to about 30 $hr^{-1}$ (specifically about 8 to about 17 $hr^{-1}$, more specifically about 10 to about 15 $hr^{-1}$).

Further, in the hydrogenation process according to one embodiment, the conversion of HMF is at least about 90% (specifically, at least about 93%, more specifically at least about 97%), and the selectivity of BHMF is, for example, at least about 90% (specifically at least about 93%, more specifically at least about 95%).

Meanwhile, according to an exemplary embodiment, after the hydrogenation is completed, the used copper/alumina catalyst can be recycled. Since the catalyst used in this embodiment is highly stable and is thus advantageous in terms of recyclability, it can be effectively applied not only to a batch mode but also to a continuous mode. Further, even after recovering the used catalyst, the initial activity level can be recovered through simple treatment.

Use of BHMF

BHMF converted through hydrogenation of HMF as described above can be utilized for various applications.

By way of example, BHMF applied as an intermediate for compound synthesis may be subjected to a subsequent reaction. For example, it can be converted to 2,5-bis (alkoxymethyl)furan (BAMF) by an etherification reaction in the presence of a solid acid catalyst. In the above embodiment, the etherification catalyst of BHMF may be, as a solid acid catalyst, a catalyst including a Bronsted acid or Lewis acid functional group linked on an organic or inorganic support (for example, an ion exchange resin such as the commercial product Amberlyst-15).

As another example, BHMF may be applied as a monomer for preparing a biomass-based polymer. A typical example of such a polymer is polyester and a polyester polymer synthesized using BHMF may replace polyethylene terephthalate (PET) or the like due to the chemical similarity between a furan ring and a phenyl ring. According to an exemplary embodiment, after reacting (esterification or transesterification) a diol monomer containing BHMF with a dicarboxylic acid, a condensation may be performed. As such, the dicarboxylic acid that can be used in combination with BHMF for the preparation of biomass-based polyester may be an aromatic dicarboxylic acid component, an aliphatic dicarboxylic acid component, or a mixture thereof. Specifically, the dicarboxylic acid may include terephthalic acid, and may further include an aromatic dicarboxylic acid, an aliphatic dicarboxylic acid and/or an alicyclic dicarboxylic acid.

According to another exemplary embodiment, BHMF can be used as a reactant for preparing polyurethane, specifically a polyurethane foam. Specifically, BHMF used as a diol compound reacts with a diisocyanate compound (e.g., IPDI, TDI and/or MDI) to form a urethane bond, and as a result, polymers having various physical properties (from brittle polymers to soft polymers) can be realized and applied to environmental and engineering fields and the like.

The present invention may be more clearly understood with reference to the following examples, and the following examples are provided only for illustrative purposes and are not intended to limit the scope of the invention.

Example

In the Examples and Comparative Examples, the prepared catalysts were analyzed according to the following analysis method.

Crystalline Phase Analysis of Catalyst

X-ray diffraction (XRD, Rigaku miniFlex300) analysis was performed using an analyzer equipped with a Cu-Kα source (30 kV and 10 mA) detector (2θ range 10-80°, scan rate 10° $min^{-1}$).

Analysis of Specific Surface Area, Pore Volume and Pore Size

BET specific surface area, pore volume and BJH pore size distribution were measured using a Micromeritics ASAP 2020. For this purpose, 100 mg of a sample was pretreated at 200° C. (heating rate of 10° C./min) in a vacuum for 2 hours, liquid nitrogen was then injected, and the properties above were analyzed through adsorption and desorption of nitrogen at 77 K.

Measurement of Copper Specific Surface Area ($N_2O$—RFC)

The copper specific surface area was measured using a $N_2O$—RFC BELCAT-B instrument (BEL Japan, Inc.).

100 mg of a sample was added, 10% $H_2$/Ar gas was injected at 30 sccm as a pretreatment process, and reduction treatment was performed in situ for 1 hour at 250° C. (heating rate of 2.5° C./min). Then, after lowering the temperature to 40° C. while flowing a He carrier gas, the amount of $N_2O$ gas that reacted with the Cu surface was measured, while flowing 1% $N_2O$/He gas at 5 sccm. Each amount of the $N_2O$ gas and $N_2$ gas generated at this time was measured, and the specific surface area of copper was measured through the amount of Cu present on the catalyst surface. The calculation of the copper specific surface area was performed based on the following two assumptions: that the reaction stoichiometric ratio of Cu/O is 2:1, and that the Cu surface density is $1.46 \times 10^{19}$ Cu atoms $m^{-2}$.

Example

Preparation of Copper/Mesoporous Alumina Catalyst by Solid-State Reaction (SSR)

The method for preparing the catalyst according to this embodiment is as shown in FIG. 1.

Referring to this figure, first, 18.01 g of an Al precursor ($Al(NO_3)_3 \cdot 9H_2O$), 12.61 g of ammonium bicarbonate ($NH_4HCO_3$), and 1.86 g of a Cu precursor (($Cu(NO_3)_2 \cdot 3H_2O$) were simultaneously physically mixed in a mortar without a solvent. Then, frictional heat was applied by continuously stirring for 21 minutes, and at this time, the solid precursors were mixed three times in total. As a result, large amount of $CO_2$ was generated, and at the same time, a gel was formed. After 13 minutes, the gel was solidified again and cured, and after 7 minutes, a gel was formed again and softened.

Then, the gel solid mixed for 21 minutes was put in a crucible and calcined for 5 hours (calcination temperature: 500° C., heating rate: 2° C./min). After calcining, the calcined product was sieved using a 200 μm metal sieve and pulverized into small pieces.

Figure 2:
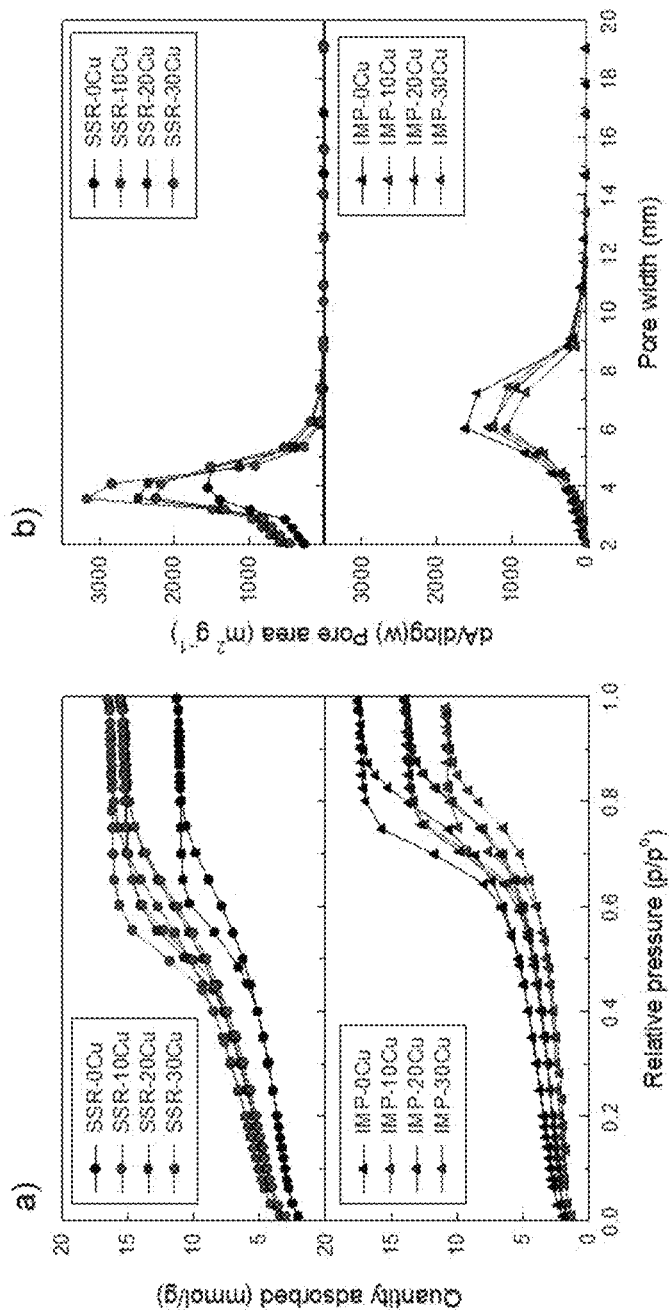
FIG. 2 shows adsorption and desorption $N_2$ isothermal curve and pore size distribution curve of the catalyst depending on the content of copper in the copper/alumina catalyst prepared according to each of Examples and Comparative Examples.

Examples and Comparative Examples, and the adsorption and desorption $N_2$ isothermal curve and pore size distribution curve according to the content of copper in the catalyst obtained through the same are shown in FIG. 2. In addition, the results of analysis of the specific surface area of the catalyst (support) and pore characteristics by BET analysis and the results of analysis of the copper specific surface area through $N_2O$—RFC are shown in Table 1 below.

TABLE 1

|  | Catalyst | Catalyst (support) specific surface area ($m^2/g$) | Pore volume ($cm^3/g$) | Pore size (nm) | Copper specific surface area ($m^2/g$) |
| --- | --- | --- | --- | --- | --- |
| Comparative Example 1 | SSR-0Cu | 300 | 0.38 | 3.8 | — |
| Comparative Example 2 | SSR-10Cu | 499 | 0.57 | 3.6 | 7.5 |
| Example 1 | SSR-20Cu | 450 | 0.53 | 3.7 | 16.0 |
| Example 2 | SSR-30Cu | 432 | 0.54 | 3.8 | 14.2 |
| Comparative Example 3 | IMP-0Cu | 280 | 0.60 | 6.2 | — |
| Comparative Example 4 | IMP-10Cu | 248 | 0.53 | 6.3 | 8.0 |
| Comparative Example 5 | IMP-20Cu | 223 | 0.48 | 6.2 | 5.5 |
| Comparative Example 6 | IMP-30Cu | 170 | 0.37 | 6.2 | 4.5 |

Subsequently, the pulverized calcined product was subjected to reduction treatment using hydrogen (reduction temperature: 300° C., heating rate: 5° C./min, reduction treatment time: 2 hours), and the reaction activity of the catalyst was analyzed and compared. The copper/mesoporous alumina catalyst prepared according to this Example was designated as SSR-20Cu (20: wt % of Cu in the catalyst weight).

Meanwhile, copper/mesoporous alumina catalysts were prepared according to the procedure described above while changing the amount of copper supported, and the prepared catalysts are designated as SSR-10Cu, SSR-20Cu and SSR-30Cu, respectively.

Comparative Example

Preparation of Copper/Gamma-Alumina Catalyst by Impregnation (IMP)

A copper precursor solution, obtained by dissolving 4.80 g of a Cu precursor ($Cu(NO_3)_2 \cdot 3H_2O$) in distilled water, was physically supported on 5 g of commercial $\gamma$-$Al_2O_3$ through impregnation, dried in an oven at 105° C., and then subjected to calcination, sieving and reduction treatment in the similar manner to Example 1, and the reaction activity was compared with that of the reduced catalyst. The catalyst prepared according to Comparative Example was designated as IMP-20Cu (20: wt % of Cu in the catalyst weight).

Meanwhile, copper/gamma-alumina catalysts were prepared according to the procedure described above while changing the amount of copper supported, and the prepared catalysts are designated as IMP-5Cu, IMP-10Cu, IMP-20Cu and IMP-30Cu, respectively.

Catalyst Analysis

Analysis of Pore Characteristics of Catalyst

An $N_2$ physical adsorption experiment was performed on the copper/alumina catalyst prepared according to each of In analyzing the properties of the catalyst, the specific surface area is an essential consideration because it is heavily dependent on the degree of dispersion of the metal. In consideration thereof, all catalysts were analyzed after calcining at 500° C.

As can be seen from Table 1 above, the specific surface areas of the catalysts (Comparative Examples 1 and 3) on which Cu was not supported were substantially similar at 300 $m^2/g$ and 280 $m^2/g$, respectively. Meanwhile, when the content of CuO in the catalyst was 20% by weight and 30% by weight, the catalysts prepared according to Examples (Examples 1 and 2) had specific surface areas of 450 $m^2/g$ and 432 $m^2/g$, respectively, representing an approximately 1.5-fold increase.

Meanwhile, the catalysts prepared according to the impregnation method (Comparative Examples 5 and 6) had specific surface areas of 223 $m^2/g$ and 170 $m^2/g$, respectively, which are low compared to the specific surface area of (280 $m^2/g$) of a gamma-alumina catalyst on which Cu was not supported (Comparative Example 3). Similar to the results of the BET specific surface area analysis, the catalyst prepared using a solid-state reaction (Example 1, SSR-20Cu) had the highest copper specific surface area of 16.0 $m^2/g$, among the catalysts that were analyzed.

Referring to FIG. 2A, the catalyst (Example) prepared through the solid-state reaction after calcination exhibits type IV isotherm having a complex of H2 and H3 hysteresis loop exhibiting typical mesoporosity (pore size: 3.8 nm) and ink-bottle-type or channel-type pore connections. In addition, as shown in Table 1, it can be seen from the graph that the specific surface area of the alumina support in the catalyst according to Comparative Example 1 is 300 $m^2/g$, which is not substantially different from the specific surface area of gamma-alumina (280 $m^2/g$), but is very different from the specific surface area of the supported copper catalyst.

FIG. 2B shows the width distribution of pores, and shows that the catalyst prepared according to the solid-state reaction of Examples have pores with a width of about 3.6 to about 3.8 nm. In contrast, the catalyst prepared by impregnation according to Comparative Example was observed to have pores with a width of about 6.2 to about 6.3 nm. Accordingly, the catalysts prepared according to Examples have smaller pores and larger specific surface areas, and this tendency is maintained even when the amount of copper that is supported is increased to 20% by weight or 30% by weight.

XRD Analysis

Figure 3:
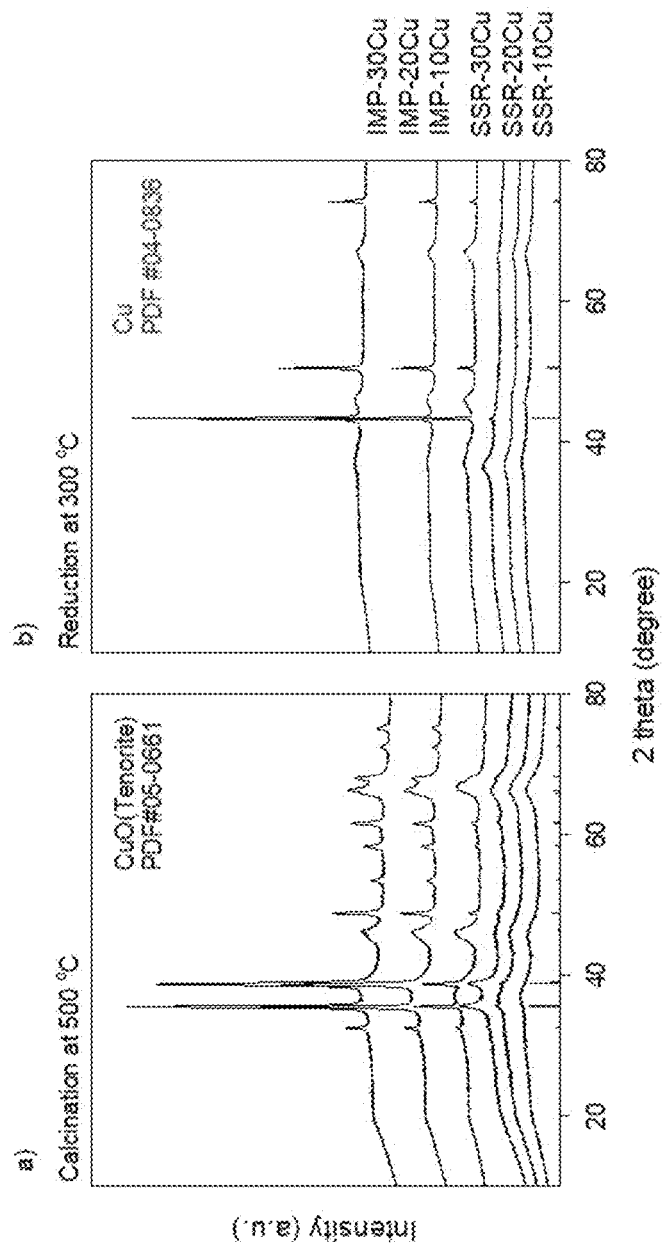
FIG. 3 shows the result of XRD analysis of a copper/alumina catalyst prepared according to each of Examples and Comparative Examples after heat treatment (calcination) and subsequent reduction treatment.

Through XRD analysis, the crystalline states of the catalysts prepared according to Examples and Comparative Examples after calcination and after reduction were analyzed and compared. The results are shown in FIG. 3 (FIG. 3A shows the result of XRD analysis of the calcined catalyst, and FIG. 3B shows the result of XRD analysis of the reduced catalyst).

As can be seen from the drawing, the catalyst prepared through the solid-state reaction of Example exhibits a low intensity of the peak corresponding to the CuO crystal state and low intensity of the peak corresponding to the Cu crystal state after reduction, compared to the catalyst prepared through impregnation of Comparative Example. That is, it can be seen that the size difference of the crystal state of the catalyst after reduction is greater than the size difference of the crystal state of the catalyst after calcination. This suggests that the catalyst prepared by solid-state reaction has copper particles that have a relatively small size and are evenly dispersed over a large surface of the support. Meanwhile, CuO and Cu peaks can be observed through XRD analysis, so the Cu particle size can be calculated by applying the same to the Bragg equation ($2d*\sin\theta=n\lambda$). In FIG. 3A, the Cu particle size was calculated using a CuO (111) plane having a $2\theta$ value of 38.7°, and the results are summarized in Table 2 below.

TABLE 2

| | Catalyst | Copper particle size (nm) |
| --- | --- | --- |
| Comparative Example 1 | SSR-10Cu | N/A |
| Example 1 | SSR-20Cu | 1.46 |
| Example 2 | SSR-30Cu | 9.07 |
| Comparative Example 2 | IMP-10Cu | 23.4 |
| Comparative Example 3 | IMP-20Cu | 17.8 |
| Comparative Example 4 | IMP-30Cu | 18.0 |

As can be seen in the above table, in the case of SSR-10Cu, the observed CuO peak was very small, and the copper particle size could not be calculated. On the other hand, it can be seen that the catalyst prepared by the solid-state reaction as in Example exhibited a remarkably decreased copper particle size compared to the catalyst prepared by impregnation.

Evaluation of Hydrogenation Catalytic Activity According to Synthesis Method

For each of the catalysts prepared according to Examples and Comparative Examples, HMF hydrogenation activity was measured according to the following procedure.

During the hydrogenation reaction, 15 g of ethanol as a solvent, 500 mg of HMF and 100 mg of a catalyst were mixed, and then hydrogenation was performed with a stirring rate of 900 RPM at a reaction temperature of 70° C. under a hydrogen pressure of 50 bar for 3.5 hours. The results are shown in Table 3 below.

TABLE 3

| | Synthesis method | Name of catalyst | HMF conversion (%) | BHMF selectivity (%) | BHMF yield (%) |
| --- | --- | --- | --- | --- | --- |
| Comparative Example 1 | SSR | SSR-10Cu | 76.8 | 98.3 | 75.5 |
| Example 1 | | SSR-20Cu | 99.1 | 99.5 | 98.6 |
| Example 2 | | SSR-30Cu | 99.8 | 99.2 | 99.0 |
| Comparative Example 2 | IMP | IMP-5Cu | 98.2 | 98.6 | 96.8 |
| Comparative Example 3 | | IMP-10Cu | 81.2 | 98.8 | 80.2 |
| Comparative Example 4 | | IMP-20Cu | 73.2 | 98.6 | 72.3 |
| Comparative Example 5 | | IMP-30Cu | 54.9 | 98.2 | 53.9 |

As can be seen in the above table, the catalysts prepared through solid-state reaction and impregnation each have distinct catalytic activities.

When the amount of Cu that was supported was 10% by weight (Comparative Example 1) in the solid-state reaction, the yield of BHMF was 75.5%, which is relatively low, but when the amount of Cu that was supported was gradually increased to 20% by weight (Example 1) and 30% by weight (Example 2), the yield of BHMF also increased rapidly, to 98.6% and 99.0%. On the other hand, the IMP-5Cu catalyst, supporting a small amount of Cu, as a catalyst prepared by impregnation (Comparative Example 2), had a high BHMF yield of 96.8%. However, as the amount of Cu that was supported gradually increased to 10% by weight, 20% by weight and 30% by weight, the BHMF yield gradually decreased to 80.2%, 72.3% and 53.9%.

Typically, as the amount of active metal that is supported increases, the degree of dispersion of the metal decreases and the catalytic activity tends to decrease. However, it is noteworthy that the catalyst prepared through a solid-state reaction exhibited rather high reaction activity even at a high amount of copper supported thereon.

The result of evaluation of hydrogenation activity according to this example showed that the catalyst having the best catalytic activity among the catalysts prepared through solid-state reaction was the SSR-20Cu catalyst.

Figure 4:
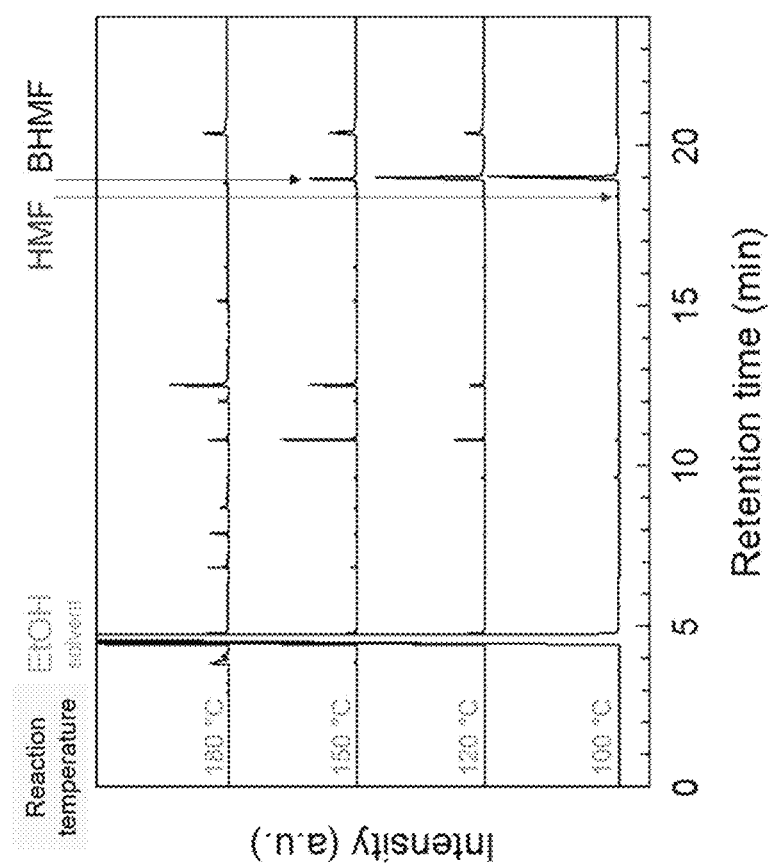
FIG. 4 shows the result of gas chromatography (GC) analysis of a product depending on the reaction temperature during hydrogenation of HMF in Examples.

Evaluation of Catalytic Activity Depending on Hydrogenation Reaction Temperature The hydrogenation activity of the catalyst depending on the reaction temperature was evaluated. At this time, the results of the hydrogenation according to the change of the reaction temperature for fixed reaction times of 3.5 hours and 15 hours, respectively, and using, as the hydrogenation catalyst, the SSR-20Cu catalyst, which was evaluated to have the best activity in the previous examples, are shown in Table 4 below. The results of gas chromatography (GC) analysis of the product are shown in FIG. 4.

TABLE 4

| Reaction time | Example | Reaction temperature (° C.) | Name of catalyst | HMF conversion (%) | BHMF selectivity (%) | BHMF yield (%) |
|---|---|---|---|---|---|---|
| 3.5 hours | Example 1 | 50 | SSR-20Cu | 28.0 | 13.0 | 3.7 |
| | Example 2 | 60 | SSR-20Cu | 73.5 | 88.7 | 65.2 |
| | Example 3 | 70 | SSR-20Cu | 99.1 | 99.5 | 98.6 |
| | Example 4 | 100 | SSR-20Cu | 98.7 | 99.1 | 97.9 |
| 15 hours | Example 5 | 100 | SSR-20Cu | 99.8 | 94.7 | 93.6 |
| | Example 6 | 120 | SSR-20Cu | 99.5 | 65.6 | 65.2 |
| | Example 7 | 150 | SSR-20Cu | 99.9 | 19.8 | 19.7 |
| | Example 8 | 180 | SSR-20Cu | 100 | 0.52 | 0.52 |

As can be seen in the above table, when the hydrogenation temperature is less than 70° C., HMF conversion is insufficient, and the yield of the target product, BHMF, is generally low. On the other hand, when the hydrogenation was performed at a reaction temperature of 100° C. or higher for a reaction time of 15 hours, generation of byproducts other than BHMF increased remarkably. In particular, it can be seen that, when the reaction temperature was increased to 180° C., the yield of BHMF was greatly reduced (0.5%), and mostly byproducts were formed. When the hydrogenation temperature was set to 70° C. in the test above, the best results could be obtained.

Evaluation of Catalytic Activity According to Amount of Catalyst

Hydrogenation of HMF was performed for 3.5 hours in the presence of a SSR-20Cu catalyst. At this time, the catalytic activity was evaluated while performing the reaction by fixing the amount of HMF, as a reactant, at 500 mg and changing the amount of the catalyst. The results are shown in Table 5 below.

TABLE 5

| | Amount of catalyst (mg) | Catalyst | HMF conversion (%) | BHMF selectivity (%) | BHMF yield (%) |
|---|---|---|---|---|---|
| Example 1 | 25 | SSR-20Cu | 39.6 | 96.3 | 38.2 |
| Example 2 | 50 | SSR-20Cu | 74.7 | 98.5 | 73.6 |
| Example 3 | 100 | SSR-20Cu | 99.1 | 99.5 | 98.6 |
| Example 4 | 250 | SSR-20Cu | 99.6 | 99.2 | 98.7 |

As can be seen in the above table, the conversion of HMF was 99% or more when the amount of catalyst in the reaction medium was 100 mg or more, and the BHMF yield was also a high value of 98% or more. On the other hand, when the amount of catalyst added was less than the certain level, the yield decreased. It was found that the amount of catalyst suitable for excellent selective hydrogenation activity under these test conditions was 100 mg, which corresponds to 20% by weight of HMF as the reactant.

Evaluation of Catalytic Activity According to Hydrogenation Pressure

Hydrogenation of HMF was performed for 3.5 hours in the presence of a SSR-20Cu catalyst. At this time, the reaction was performed and the catalytic activity was evaluated while the hydrogen pressure was changed. The results are shown in Table 6 below.

TABLE 6

| | Hydrogen pressure (bar) | Catalyst | HMF conversion (%) | BHMF selectivity (%) | BHMF yield (%) |
|---|---|---|---|---|---|
| Example 1 | 10 | SSR-20Cu | 24.5 | 94.3 | 23.1 |
| Example 2 | 20 | SSR-20Cu | 97.0 | 90.6 | 87.9 |
| Example 3 | 30 | SSR-20Cu | 97.5 | 98.1 | 95.7 |
| Example 4 | 50 | SSR-20Cu | 99.1 | 99.5 | 98.6 |

As can be seen in the above table, the BHMF yield at a hydrogen pressure of 20 bar or more was about 87.9% or more, which was relatively high. On the other hand, when the hydrogen pressure was 10 bar, the BHMF yield was greatly decreased to 23.1%. Therefore, it can be seen that hydrogen pressure of a certain level or higher is required in order to obtain BHMF from HMF at a high yield. For this test, a hydrogen pressure of about 50 bar was appropriate.

Evaluation of Catalytic Activity According to Reaction Medium

Hydrogenation of HMF was performed for 3.5 hours in the presence of the SSR-20Cu catalyst. At this time, the reaction was performed while changing reaction media and the catalytic activity was evaluated. The results are shown in Table 7 below.

TABLE 7

| | Solvent | Catalyst | HMF conversion (%) | BHMF selectivity (%) | BHMF yield (%) |
|---|---|---|---|---|---|
| Example 1 | Methanol | SSR-20Cu | 92.2 | 96.8 | 93.2 |
| Example 2 | Ethanol | SSR-20Cu | 99.1 | 99.5 | 98.6 |
| Example 3 | Butanol | SSR-20Cu | 74.0 | 92.6 | 68.5 |
| Example 4 | Ethyl acetate | SSR-20Cu | 52.8 | 95.3 | 50.3 |
| Example 5 | Hexane | SSR-20Cu | 0.0 | 0.0 | 0.0 |
| Example 6 | THF | SSR-20Cu | 9.0 | 83.5 | 7.7 |

When ethanol was used as the reaction medium, the yield of BHMF was the highest (98.6%). On the other hand, it can be seen that, when hexane and THF, which are nonpolar solvents, are used, catalytic activity was low. Therefore, when using the Cu/alumina catalyst prepared in Examples, it was found that it is preferable to use a polar solvent, particularly alcohol, as a reaction medium under test conditions.

Evaluating Moldability of Catalyst

Figure 5:
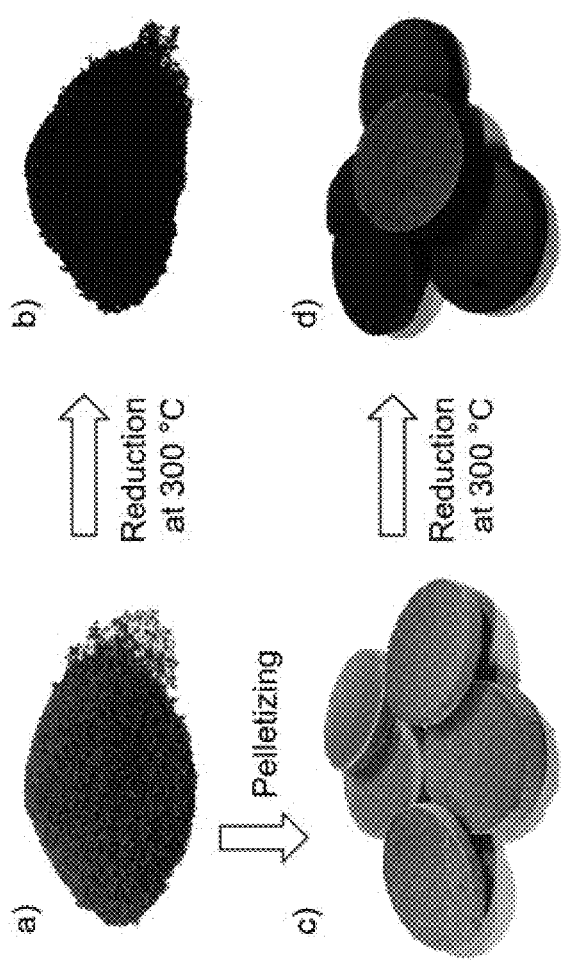
FIG. 5 is an image showing the appearance of the copper/alumina catalyst prepared in the form of a powder and a molded product according to Example.

It was evaluated whether or not the copper/alumina catalyst prepared according to Examples could be prepared in the form of a molded product suitable for commercialization. At this time, the molding catalyst was prepared using a pelletizer (PIKE Technologies, CrushIR), and the molding conditions were 4.5 to 5 tons. The results are shown in FIG. 5.

As can be seen from the drawing, the copper/alumina catalyst could be relatively easily molded into pellets, because alumina, when present in a large amount, has the property of acting as a binder, and the shape of the molded product was maintained even when reduction treatment for activation was performed prior to the hydrogenation reaction.

According to an embodiment of the present disclosure, the copper-supported alumina catalyst has a small pore size and a high specific surface area, as well as nano-sized copper particles uniformly distributed on the support, compared to a catalyst prepared by any conventional liquid-based method such as impregnation. In particular, it can be prepared by performing a single-step reaction in a simple manner of applying physical or mechanical external energy, through a method such as milling, to a feedstock mixture including a copper precursor and an alumina precursor, without the use of a solvent. The catalyst thus prepared can confer a variety of advantages, for example, can overcome the technical limitations of the liquid-state method, such as impregnation (or a two-step catalyst preparation method), which makes it time-consuming and expensive to produce the catalyst, can be easily prepared in the form of a molded product, which is advantageous for commercialization, and can provide catalytic activity capable of effectively converting a biomass-derived furan-based compound such as HMF to BHMF, even at a low temperature.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for preparing bis-2,5-hydroxymethylfuran (BHMF) from 5-hydroxymethylfurfural (HMF) comprising:
   feeding a feedstock comprising 5-hydroxymethylfurfural (HMF); and
   hydrogenating the feedstock in a liquid reaction medium using a catalyst containing a mesoporous alumina-containing support and particles of copper as an active metal on the mesoporous alumina-containing support to convert the 5-hydroxymethylfurfural (HMF) in the feedstock to bis-2,5-hydroxymethylfuran (BHMF),
   wherein the catalyst has (i) a copper particle size of 15 nm or less, (ii) a copper content of 15 to 40% by weight based on the element, and (iii) a copper specific surface area ($S_{Cu}$) of 6 to 35 m$^2$/g, and (iv) a pore size of 2 to 6 nm.

2. The method according to claim 1, wherein the liquid reaction medium is a polar solvent,
   wherein the polar solvent comprises at least one selected from the group consisting of water and alcohol having 5 or fewer carbon atoms.

3. The method according to claim 1, wherein a weight ratio of the HMF:the liquid reaction medium is in the range of 1:10 to 1:50, and
   a weight ratio of the HMF:the catalyst is 1:0.05 to 1:0.8.

4. The method according to claim 1, wherein the hydrogenation is performed at a reaction temperature of 60 to 110° C. and a hydrogen pressure of 15 to 100 bar.

5. The method according to claim 1, further comprising converting the BHMF obtained through the hydrogenation to 2,5-bis(alkoxymethyl)furan (BAMF) by etherification.

6. The method according to claim 1, further comprising:
   esterifying or transesterifying a diol monomer containing the BHMF obtained through the hydrogenation with a dicarboxylic acid component; and
   polycondensing the esterification or transesterification product.

7. The method according to claim 1, further comprising reacting the diol monomer containing the BHMF obtained through the hydrogenation with a diisocyanate compound to form a urethane bond.

8. The method according to claim 1, wherein the catalyst is prepared by the following process comprising:
   a) performing a solid-state reaction in the absence of a solvent while applying external energy to a mixture containing at least one alumina precursor, at least one copper precursor and a base to form a catalytic solid in a form of a gel, and
   b) thermally treating the catalytic solid under an oxygen-containing atmosphere at a temperature of 300 to 800° C. to support copper particles in a form of oxide on a mesoporous alumina-containing support.

9. The method according to claim 8, wherein the process further comprises c) reducing the copper particles in the form of oxide obtained in step b).

10. The method according to claim 8, wherein the copper precursor is an organic or inorganic acid salt of copper, a complex of copper, or a combination thereof.

11. The method according to claim 10, wherein the copper precursor comprises at least one selected from the group consisting of copper hydroxide phosphate, copper nitrate, copper sulfate, copper acetate, copper formate, copper (II) chloride, and copper iodide.

12. The method according to claim 8, wherein the alumina precursor is an organic or inorganic acid salt of aluminum, an alkoxide of aluminum, a complex of aluminum, or a combination thereof.

13. The method according to claim 12, wherein the alumina precursor comprises at least one selected from the group consisting of aluminum acetate, aluminum acetylacetonate, aluminum bromide, aluminum t-butoxide, aluminum sec-butoxide, aluminum pentoxide, aluminum ethoxide, aluminum isopropoxide, aluminum tributoxide, aluminum chloride, aluminum bromide, aluminum iodide, aluminum sulfate, aluminum nitrate, and a hydrate thereof.

14. The method according to claim 8, wherein the base comprises at least one selected from the group consisting of ammonium carbonate, ammonium bicarbonate, ammonium chloride, ammonium oxalate, ammonium sulfate, ammonium hydroxide, ammonium nitrate, lithium hydroxide, sodium hydroxide, potassium hydroxide, calcium hydroxide and magnesium hydroxide.

15. The method according to claim 8, wherein a molar ratio of the copper precursor to the base in step a) is 0.02 to 0.1.

16. The method according to claim 1, wherein the catalyst has a specific surface area (BET) of 330 to 700 m$^2$/g.

17. The method according to claim 1, wherein a degree of dispersion of copper in the catalyst is 4 to 16%.

18. The method according to claim 1, a pore volume of the mesoporous support in the catalyst is 0.3 to 0.8 cm$^3$/g.

19. The method according to claim 1, wherein the catalyst is a molded catalyst having a ball shape, a tablet shape, a granule shape, a pellet shape, or a cylindrical shape.

* * * * *